US006185344B1

(12) United States Patent
Bevenot et al.

(10) Patent No.: US 6,185,344 B1
(45) Date of Patent: Feb. 6, 2001

(54) OPTICAL DEVICE FOR DETECTING TRACES OF GASEOUS HYDROGEN IN SITU IN AN ENVIRONMENT AT CRYOGENIC TEMPERATURES

(75) Inventors: Xavier Bevenot, Saint-Etienne; Michel Clement, Vernon; Henri Gagnaire, Saint-Chamond, all of (FR)

(73) Assignee: Societe National d'Etude de Construction de Moteurs D'Aviation-S.N.E.C.M.A., Paris (FR)

( * ) Notice: Under 35 U.S.C. 154(b), the term of this patent shall be extended for 0 days.

(21) Appl. No.: 09/221,567

(22) Filed: Dec. 28, 1998

(30) Foreign Application Priority Data

Dec. 29, 1997 (FR) .................................................. 97 16614

(51) Int. Cl.[7] .................................................... G02B 6/00
(52) U.S. Cl. ................................................. 385/12; 385/14
(58) Field of Search .................................... 385/1–5, 9–14

(56) References Cited

PUBLICATIONS

Butler, M.A., "Micromirror Optical–Fiber Hydrogen Sensor", Sensors and Actuators B, vol. B22, No. 2, Nov. 1, 1994 pp. 155–163.

Wang, et al., "Research of Fiber–Optic Hydrogen Sensor", Proceedings of the SPIE: Second International Symposium Measurement Technology and Intelligent Instruments Wuhan, China, 10/11, 1993 vol. 2101, No. 2, pp. 1139–1141.

*Primary Examiner*—Robert Kim
(74) *Attorney, Agent, or Firm*—Weingarten, Schurgin, Gagnebin & Hayes LLP

(57) ABSTRACT

The optical device for detecting in situ traces of gaseous hydrogen in an environment at cryogenic temperature, using a sensor having a fine film of palladium whose optical properties vary as a function of the concentration of hydrogen in contact with the film comprises, a palladium micromirror deposited in the form of a film at a first end of a first optical fiber, a first light source emitting a light signal at a predetermined wavelength into a second end of the first optical fiber, and means for detecting the light signal as modified after passing in contact with the palladium micromirror disposed in the environment at cryogenic temperature, processor circuits for responding to variation in the intensity of the light signal contacting the palladium micromirror to determine hydrogen concentration, and means for localized heating of the palladium micromirror, by light radiation so as to keep the palladium of the micromirror in its α phase.

10 Claims, 1 Drawing Sheet

OPTICAL DEVICE FOR DETECTING TRACES OF GASEOUS HYDROGEN IN SITU IN AN ENVIRONMENT AT CRYOGENIC TEMPERATURES

FIELD OF THE INVENTION

The present invention relates to an optical device for detecting traces of gaseous hydrogen in situ in an environment at cryogenic temperatures by using a sensor which comprises a fine film of palladium whose optical properties vary as a function of the concentration of hydrogen in contact with the film.

PRIOR ART

The use of micromirror hydrogen sensors is already known for detecting hydrogen close to the explosive threshold, i.e. at a concentration of about 4% in air.

Such sensors comprise a medium such as an optical fiber having cladding and a core with a film of palladium deposited on the end of the fiber by evaporation. In the presence of hydrogen, the film transforms into a hydride of the form $PdH_x$. The effect of a change in the concentration of hydrogen is to change the composition of the hydride (by varying x) and also to change the electron structure thereof, thus giving rise to a change in the reflectivity of the film. By measuring the light it reflects, it is possible to deduce the concentration of hydrogen.

Such sensors have been recommended for use at ambient temperature or at temperatures greater than ambient.

However, when such sensors are implemented under operating conditions that are conventional but in environments that are at cryogenic temperature, they do not enable satisfactory sensitivity or sufficiently short response times to be obtained.

OBJECT AND BRIEF DESCRIPTION OF THE INVENTION

The present invention seeks to remedy the above-mentioned drawbacks and to enable traces of gaseous hydrogen present in an environment at cryogenic temperature, e.g. about 20 K to 80 K to be detected reliably, with a short response time and with satisfactory sensitivity by means of a device that is compact and located in situ.

According to the invention, these objects are achieved by an optical device for in situ detection of traces of gaseous hydrogen in an environment at cryogenic temperature, using a sensor having a fine film of palladium whose optical properties vary as a function of the concentration of hydrogen in contact with the film, the device comprising a palladium micromirror deposited in the form of a film at a first end of a first optical fiber, a first light source emitting a light signal at a predetermined wavelength into a second end of the first optical fiber, means for detecting the light signal as modified after passing in contact with the palladium micromirror that is disposed in the environment at cryogenic temperature, processor circuits for responding to variation in the intensity of the light signal that has been in contact with the palladium micromirror to determine the hydrogen concentration, and localized heating means for heating the palladium micromirror by light radiation, so as to maintain the micromirror in the α phase of palladium.

In a first embodiment, the device comprises a first light source constituted by a laser diode of wavelength $\lambda_1$ situated in the near infrared and of power that is less than a few tens of milliwatts for emitting a detection signal via a Y coupler into said second end of the first optical fiber so as to illuminate the rear face of the palladium micromirror, the Y coupler receiving in return the light signal of wavelength $\lambda_1$ reflected by the palladium micromirror and applying said reflected light signal via an interference filter to said detector means, and the means for localized heating of the palladium micromirror by light radiation comprise a second light source constituted by a laser diode of wavelength $\lambda_2$ situated in the infrared, longer than the wavelength $\lambda_1$ and continuously emitting a beam of power lying in the range a few tens to several hundreds of milliwatts, into a first end of a second optical fiber whose second end is situated at a short distance from the palladium micromirror in the environment at cryogenic temperature so as to heat the front face of the micromirror by the light radiation from the second light source and the second optical fiber.

More particularly, the first end of the first optical fiber and the second end of the second optical fiber are united by a ferrule of transparent material provided with orifices for communication with the environment at cryogenic temperature.

In a second embodiment, the device comprises a first light source constituted by a laser diode of wavelength $\lambda$ situated in the infrared and of power lying in the range a few tens of milliwatts to several hundreds of milliwatts for continuously emitting a detection signal via a Y coupler into said second end of the first optical fiber to illuminate the rear face of the palladium micromirror while simultaneously applying localized heating to said rear face, the Y coupler receiving in return the light signal of wavelength $\lambda$ as reflected by the palladium micromirror and applying said reflected light signal to said detection means.

In a third embodiment, the device comprises a first light source constituted by a laser diode of wavelength $\lambda$ situated in the infrared and of power lying in the range a few tens of milliwatts to several hundreds of milliwatts for continuously emitting a detection signal via an optical isolator into said second end of the first optical fiber to illuminate the rear face of the palladium micromirror situated at the first end of the first optical fiber, thereby providing localized heating of said rear face, the light signal of wavelength $\lambda$ being transmitted through the semitransparent palladium micromirror to a first end of a second optical fiber placed facing the second end of the first optical fiber carrying the palladium micromirror, the second optical fiber having a core of diameter that is equivalent to or greater than the core diameter of the first optical fiber, and, at its second end, applying the light signal transmitted through the palladium micromirror to said detection means.

Advantageously, under such circumstances, adhesive fixes the first optical fiber close to its first end to a transparent support provided with orifices for communicating with the environment at cryogenic temperature, and adhesive also fixes the second optical fiber close to its first end to the support in such a manner that the distance between the first end of the first fiber and the first end of the second fiber is of the order of a few tens of micrometers.

The environment at cryogenic temperatures can be constituted by a gaseous atmosphere, such as nitrogen, or by a liquid fluid such as a cooling oil.

The device of the invention can be applied in particular in space, e.g. to detecting leaks of hydrogen inside the lagging of lines for conveying propellant in a launcher.

BRIEF DESCRIPTION OF THE DRAWING

Other characteristics and advantages of the invention appear from the following description of particular embodiments, given as examples and with reference to the accompanying drawing, in which.

DETAILED DESCRIPTION OF PARTICULAR EMBODIMENTS

Figure 1:
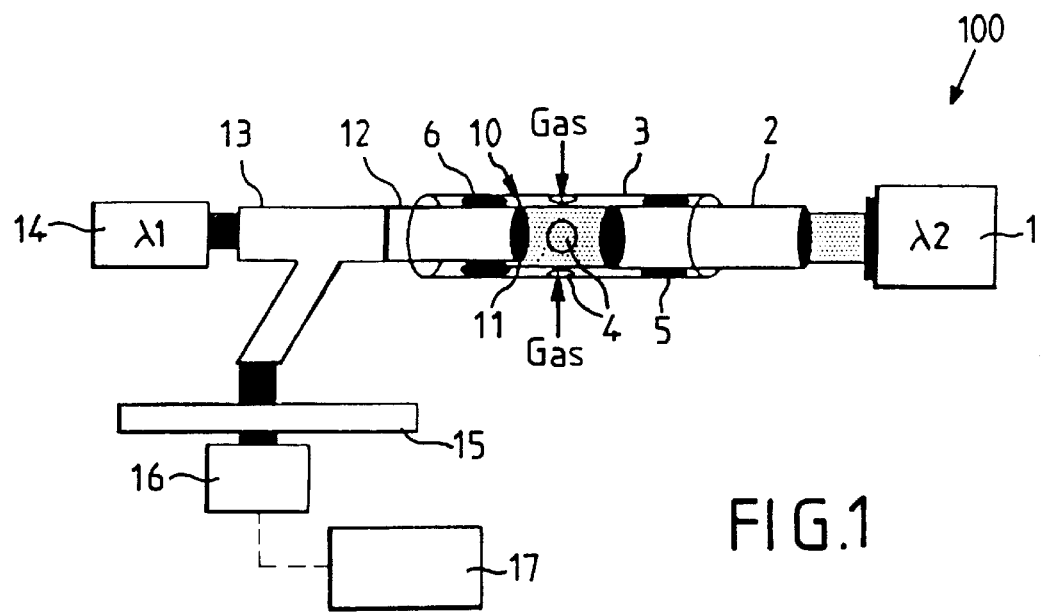
FIG. 1 is a diagrammatic view of a first embodiment of the invention showing an example of an optical device with two light sources for detecting gaseous hydrogen.

Consideration is given initially to the embodiment of FIG. 1, which shows a first optical fiber 12 having one end covered in a palladium metal film constituting a semitransparent micromirror. The palladium micromirror 11 constitutes the active element of the sensor 10 in contact with a surrounding medium in which gaseous hydrogen might be present and needs to be detected, even at trace concentrations.

The optical fiber 12 whose first end has the palladium micromirror 11 deposited thereon may, for example, have a core diameter of about 50 micrometers ($\mu$m) and a cladding diameter of about 125 $\mu$m.

The palladium micromirror 11 may be constituted by a film of thickness lying in the range 10 nanometers (nm) to 50 nm, and preferably lying in the range 15 nm to 30 nm.

The second end of the optical fiber 12 is itself connected to a Y coupler 13 whose main branch receives a light beam from a laser diode 14 at a power of less than a few tens of milliwatts, and emitting a light signal of wavelength $\lambda_1$ that is situated in the near infrared. The side branch of the Y coupler 13 which receives the light returned by the micromirror 11 via the optical fiber 12 directs said reflected light to a detector 16 via an interference filter 15 whose role is explained below.

The laser beam emission module comprising the laser diode 14 can be set apart from the measurement zone which is situated in an environment at cryogenic temperature, by using an optical fiber connected to the main branch of the Y coupler 13.

Similarly, the interference filter 15 and the detector 16 together with the circuits 17 for processing signals from the detector 16 can be outside the measurement zone which is situated in an environment at cryogenic temperature, by using an optical fiber connected to the side branch of the Y coupler 13 for receiving the light signal reflected by the micromirror 11.

The detector 16 which can be constituted by a radiometer or any other device for measuring light power and adapted to the power from the laser diode 14 provides in real time information concerning the light power reflected by the micromirror 11, said information being given to the processor circuits 17 which may comprise a digital or an analog acquisition system. By measuring the reflected light, it is possible to deduce the concentration of hydrogen in the medium which is in contact with the micromirror 11, providing the hydrogen in contact with the micromirror 11 gives rise to a hydride PdH$_x$ whose composition is a function of hydrogen concentration, thereby determining reflectivity which varies in a manner that is determined, reversible, and reproducible, as a function of hydrogen concentration.

In general, the greater the concentration of hydrogen, the faster and more marked the response of the palladium micromirror sensor 11. Furthermore, fractional variations in the reflectivity of a film of PdH$_x$ as a function of hydrogen concentration show that the opaqueness of the film increases rapidly up to 2% hydrogen concentration, and then increases more slowly for hydrogen concentration varying in the range 2% to 100%. The linearity of the curve giving the variations in fractional reflectivity as a function of hydrogen concentration is nevertheless completely linear over the range 2% to 100% concentration of hydrogen. The detection system of the invention thus makes it possible not only to detect, but also (after calibration) to evaluate the concentration of hydrogen on the basis of a measurement of the quantity of light that is reflected back by the micromirror 11.

When detecting traces of hydrogen, particularly when it is appropriate to detect or evaluate hydrogen concentrations that are below a threshold concentration (of about 4%) above which a mixture of gases containing the hydrogen becomes explosive, it turns out that a palladium micromirror sensor is satisfactory at ambient temperature or at a temperature greater than ambient.

However, response time becomes far too long (several hours) and therefore unsuitable for numerous applications when the palladium micromirror 11 is situated in a medium at cryogenic temperature, as occurs for example in rocket engines, where for reasons of safety, it is desirable to be able to detect hydrogen leaks with very short reaction times, of the order of a few seconds, e.g. in the gap between a propellant duct and the lagging of said duct.

To remedy that drawback, and to obtain short response times, the method of the invention includes localized heating of the palladium micromirror 11 so as to keep the micromirror in the $\alpha$ phase of the palladium-hydrogen system.

The palladium-hydrogen system PdH$_x$ has two phases, $\alpha$ and $\beta$, with a fairly large range in which both phases coexist:

when x<0.03, only the $\alpha$ phase exists;

when 0.03<x<0.6, both the $\alpha$ and the $\beta$ phases coexist; and when x>0.6, only the $\beta$ phase exists.

At very low temperature, e.g. at −196° C., when palladium is in contact with a medium such as nitrogen containing hydrogen at low concentration, e.g. at about 4%, then the palladium-hydrogen system is to be found in its $\beta$ phase, and the reaction time of the sensor is prohibitive, since it is of the order of several hours.

According to the invention, by applying localized heating to the palladium micromirror 11 in sufficient quantity to bring the palladium-hydrogen system into its $\alpha$ phase, the reaction time is reduced to a few seconds, and sensitivity is satisfactory.

In the embodiment of FIG. 1, the localized heating of the micromirror 11 is provided by means of a beam of coherent light applied to the front face of the micromirror 11. For this purpose, a power laser diode 1 is used that emits a light beam at a wavelength $\lambda_2$ that is situated in the infrared, and that is preferably longer than the wavelength $\lambda_1$ of the light beam emitted by the laser diode 14. Advantageously, the laser diode 1 emits a beam continuously at a power lying in the range a few tens to a few hundreds of milliwatts.

The laser diode 1 emits a light beam to a first end of an optical fiber 2 whose second end is situated at a short distance from the palladium micromirror 11 in the environment at cryogenic temperature. The optical fiber 2 can be of sufficient length or it can be made up of a series of interconnected optical fibers to ensure that the laser diode 1 can itself be located, where appropriate, outside the measurement zone in which the ambient medium is at cryogenic temperature.

As can be seen in FIG. 1, the first optical fiber 12 may be secured to a glass ferrule 3, e.g. being bonded by adhesive 6, in zones that are close to its first end carrying the micromirror 11, while the optical fiber 2 can be secured to the same ferrule 3, e.g. via an adhesive bond 5 in zones that are close to its second end located close to the micromirror 11. The glass ferrule 3 has orifices 4 for communicating with the environment at cryogenic temperature which might contain hydrogen and it serves to hold the second end of the optical fiber 2 in a position facing the end of the optical fiber 12 that is covered in the micromirror 11 so that the power light beam from the optical fiber 2 strikes the front face of the micromirror 11 directly.

A portion of the radiation emitted by the optical fiber 2 from the power diode 1 at the wavelength $\lambda_2$ passes through the micromirror 11. The interference filter 15 prevents this residual radiation of wavelength $\lambda_2$ reaching the detector 16, and thus guarantees that the detector 16 takes account only of the radiation at wavelength $\lambda_1$ as emitted by the laser diode 14 and returned by the micromirror 11.

In the device 100 of the invention as shown in FIG. 1, because the micromirror 11 absorbs locally the light energy supplied by the laser diode 1, the temperature of the metal of the micromirror 11 is locally raised so that, for example, it is possible to obtain a rise time tm (going from 10% to 90% of the final response of the sensor) that is less than 3 seconds for detecting 4% hydrogen in nitrogen (representing a flow rate of 500 Nl/h) in gas at a temperature of −196° C. The temperature of the palladium is thus raised to a temperature such that the metal is in its $\alpha$ phase. The relative change in the signal (Vr) corresponding to the atmosphere going from 100% nitrogen to x % hydrogen is a few percent when the palladium is in its $\alpha$ phase so that it is not only possible to perform detection quickly, but also reliably and with sufficient sensitivity.

By selecting a wavelength $\lambda_2$ for the heating laser diode 1 that is different from the wavelength $\lambda_1$ of the laser diode 14 which emits the detection signal, it is possible to discriminate between the two light signals in the interference filter 15 placed ahead of the detector 16. Furthermore, the wavelength $\lambda_2$ is preferably longer than $\lambda_1$ since energy absorption in the metal of the micromirror 11 increases with increasing wavelength.

Figure 2:
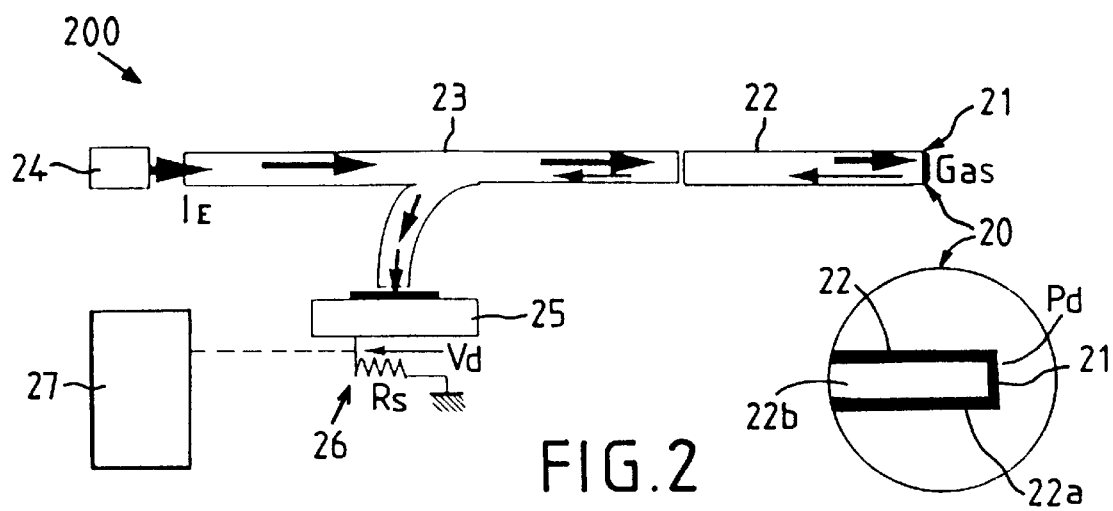
FIG. 2 is a diagrammatic view of a second embodiment of the invention comprising an optical disposition using a single light source for detecting gaseous hydrogen.

FIG. 2 shows a second embodiment of the invention in which the optical detector device 200 comprises a single light source 22 which performs the roles of both laser diodes 14 and 1 of FIG. 1 simultaneously.

In this case, the light source 24, the Y coupler 23, the optical fiber 22, and the micromirror 21 can be mounted in the same way as the corresponding elements 14, 13, 12, and 11 in FIG. 1. The elements 24, 23, 22, and 21 are therefore not described again in detail. However, the mounting is simplified in that the second laser source 1, the second optical fiber 2, and the means 3 to 6 for positioning the ends of the optical fibers 2 and 12 relative to each other are all omitted. Furthermore, in the embodiment of FIG. 2, there is no longer any need to use an interference filter such as the filter 15 of FIG. 1, so a receiver-detector 25–26 can be placed directly at the output from the side branch of the coupler 23. Signal processing circuits 27 are associated with the receiver-detector assembly 25–26.

The palladium micromirror 21 is placed at the end of the optical fiber 22 comprising both cladding 22a and a core 22b (see magnified detail of FIG. 2). The end of the optical fiber 22 and the micromirror 21 constitute a miniature end sensor 20 disposed in situ in a system where it is desirable to measure or to detect a leakage level of hydrogen. Like the sensor 10, the end sensor 20 can be placed in the immediate vicinity of interfaces or assemblies that are suspected of leaking, or it can be integrated therein. It can also be used to measure the concentration of hydrogen in an enclosure, or indeed to detect the presence of traces of hydrogen in a liquid such as an oil for cooling a process.

As with the device 100 of FIG. 1, the device 200 can include additional optical fibers connected firstly between the coupler 23 and the light source 24 and secondly between the coupler 23 and the receiver-detector 25–26, so as to enable the source 24 and the signal detection signal and processing means 25 to 27 to be offset away from the measurement zone at cryogenic temperature.

To enable the device 200 of FIG. 2 to take measurements with short rise times and satisfactory sensitivity in environments at cryogenic temperature, with performance equivalent to the performance of the device 100 of FIG. 1, it is necessary for the light source 24 to perform two functions: that of emitting a detection light signal, and that of emitting a light beam for heating the micromirror 21. That is why it is appropriate to select a light source such as a laser diode that emits a light signal continuously at a wavelength $\lambda$ which is situated in the infrared (and not the near infrared), at power lying in the range a few tens of milliwatts to several hundreds of milliwatts, so that the palladium-hydrogen system of the micromirror 21 is in its $\alpha$ phase in spite of the cryogenic temperature environment in which the sensor 20 is placed.

In the embodiment of FIG. 2, the light beam supplied by the source 24 is both a vector carrying information concerning hydrogen detection and a vector carrying energy for supplying to the palladium micromirror 21 in order to raise its temperature.

Under such circumstances, the micromirror 21 is heated via its rear face whereas in the embodiment of FIG. 1, heating was performed via the front face of the micromirror 11. In contrast, detection relies on the same principle in both embodiments of FIGS. 1 and 2, i.e. that of a light signal emitted by the source 24 and reflected by the mirror 21 which, after being diverted via the Y coupler 23, is detected by the detection assembly 25–26.

Without there being any need to use two light sources at different wavelengths, given that the power of the laser diode 24 is overdimensioned compared with the power that would be required merely for detecting a reflected signal, so as to ensure that the palladium temperature is locally raised sufficiently to enable the palladium to be in its $\alpha$ phase, the measurement device 200 is capable of detecting traces of hydrogen in a cryogenic environment under the conditions mentioned above with reference to the device 100, for example detecting 4% hydrogen in nitrogen at −196° C. with a rise time tm of less than 3 seconds and with relative variation in the signal Vr of a few percent.

Figure 3:
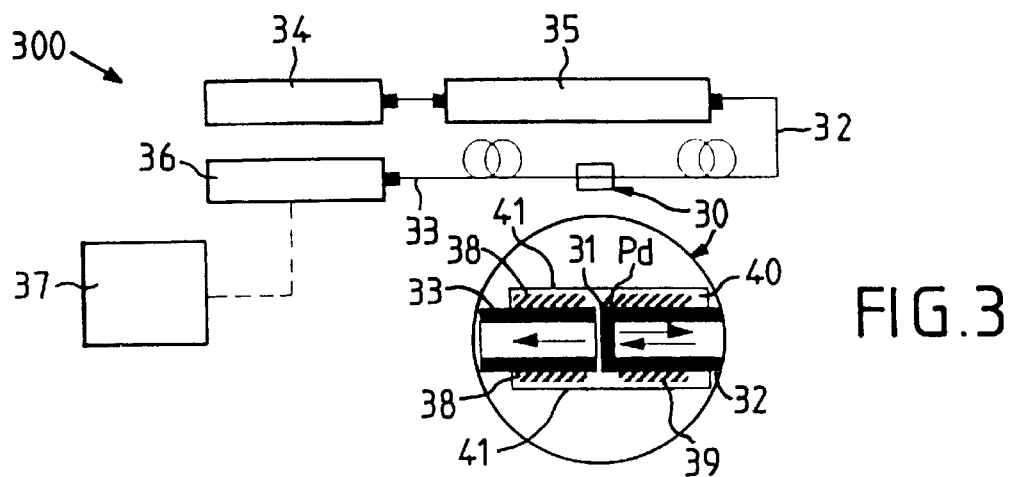
FIG. 3 is a diagrammatic view of a third embodiment of the invention comprising an optical disposition using a single light source for detecting gaseous hydrogen.

FIG. 3 shows an optical device 300 for in situ detection of traces of gaseous hydrogen in an environment at cryogenic temperature in a third embodiment of the invention, in which the presence of hydrogen is detected by measuring variation in the intensity of light that is transmitted (and not reflected) by a palladium micromirror 31 placed at the end of an optical fiber 32 receiving light from a light source 34.

The end of the optical fiber 32 that is provided with the micromirror 31 is placed facing the end of a second optical fiber 33 whose core diameter is equivalent to or greater than that of the first optical fiber 32. The second optical fiber 32 serves to transport the light signal transmitted through the micromirror 31 to a detector 36 which is associated with a signal processing system 37.

The configuration of the device shown in FIG. 3 makes it possible to avoid using a coupler, thereby reducing light losses between the light source 34 and the micromirror 31, while maximizing the power used for detecting the signal.

The power of the light source 34, constituted by a laser diode of wavelength λ situated in the infrared, must lie in the range a few tens of milliwatts to several hundreds of milliwatts, i.e., like the heating laser diodes 1 and 24 in FIGS. 1 and 2, it must be capable of causing the temperature of the micromirror 31 to be raised locally.

The use of a sensor 30 having a palladium micromirror 31 that is used in transmission thus makes it possible to maximize heating efficiency and the intensity of the signal that is used for detection.

The relative variation in the signal Vr corresponding to detecting 4% hydrogen in nitrogen at cryogenic temperature, and the rise time tm are similar in value to those obtained under the same conditions of use with a sensor 10 or 20 used in reflection.

It may be observed that the micromirror 31 reflects in undesirable manner a certain fraction of light power to the source 34. In order to limit this drawback, an optical isolator 35 is interposed between the laser diode 34 and the optical fiber 32.

The detail on a larger scale in FIG. 3 shows an example of the sensor 30 in which the facing ends of the optical fiber 33 and of the optical fiber 32 on which the palladium micromirror 31 is deposited are held in well-defined relative positions with a spacing of the order of a few micrometers to a few tens of micrometers by means of a support 40 that is in the form of a plate or a ferrule, e.g. made of glass, which is stuck in zones 39 and 38 to the optical fibers 32 and 33 in the vicinity of the facing ends thereof, and has openings 41 for communicating with the environment at cryogenic temperature.

The sensor 30 is particularly adapted to volume detection of traces of hydrogen in an enclosure.

As in the embodiments of FIGS. 1 and 2, the elements 34, 35, and 36, 37 can be offset out of the medium at cryogenic temperature by additional optical fibers connected respectively to the optical fibers 32 and 33.

Whatever the embodiment, the detection device of the invention is of small size and weight, is insensitive to electromagnetic disturbance, and is very safe to use in an explosive medium, while nevertheless being capable of implementation at reasonable cost.

More particularly, the palladium micromirror can be heated by power laser diodes at wavelengths lying in the 670 nm to 1500 nm range. By way of example, good results have been obtained with a power laser diode having a wavelength of 810 nm.

It is mentioned above that a minimum heating light power must be applied to the palladium micromirror in order to keep it in the α phase of palladium.

It has been found that a power $P_m$ of 70 mW enables palladium to remain in its α phase for a temperature lying in the range 23° C. (or greater) and −196° C. with the concentration of hydrogen in nitrogen varying over the range 0% to 4%.

When the hydrogen concentration varies over the range 4% to 100%, a power $P_m$ in excess of 50 mW enables the palladium to be in its α phase at 23° C. The power $P_m$ required to keep the palladium in its α phase at −196° C. (for hydrogen concentrations lying in the range 4% to 100%) needs to be greater than about 350 mW.

As a function of the powers given above, the power selected for the laser diode depends mainly on light losses that exist between the source and the micromirror. When using a Y coupler that enables power to be shared symmetrically (50/50), the total loss associated with using this type of coupler and with the connection arrangements for inserting the sensor and the coupler is equal to 58%. Given such losses, in this particular configuration (particular type of fiber and of coupler), the minimum power required of the source to ensure operation in the α phase from 23° C. to −196° C. so as to be able to detect up to 4% hydrogen in nitrogen is about 170 mW. For identical operation up to 100% hydrogen, it is necessary to have a source of about 730 mW.

What is claimed is:

1. An optical device for in situ detection of traces of gaseous hydrogen in an environment at cryogenic temperature, using a sensor having a fine film of palladium whose optical properties vary as a function of the concentration of hydrogen in contact with the film, the device comprising a palladium micromirror deposited in the form of a film at a first end of a first optical fiber, a first light source emitting a light signal at a predetermined wavelength into a second end of the first optical fiber, means for detecting the light signal as modified after passing in contact with the palladium micromirror that is disposed in the environment at cryogenic temperature, processor circuits for responding to variation in the intensity of the light signal that has been in contact with the palladium micromirror to determine the hydrogen concentration, and localized heating means for heating the palladium micromirror by light radiation, so as to maintain the micromirror in the α phase of palladium.

2. A device according to claim 1, comprising a first light source constituted by a laser diode of wavelength $\lambda_1$ situated in the near infrared and of power that is less than a few tens of milliwatts for emitting a detection signal via a Y coupler into said second end of the first optical fiber so as to illuminate the rear face of the palladium micromirror, the Y coupler receiving in return the light signal of wavelength $\lambda_1$ reflected by the palladium micromirror and applying said reflected light signal via an interference filter to said detector means, and wherein the means for localized heating of the palladium micromirror by light radiation comprise a second light source constituted by a laser diode of wavelength $\lambda_2$ situated in the infrared, longer than the wavelength $\lambda_1$ and continuously emitting a beam of power lying in the range a few tens to several hundreds of milliwatts, into a first end of a second optical fiber whose second end is situated at a short distance from the palladium micromirror in the environment at cryogenic temperature so as to heat the front face of the micromirror by the light radiation from the second light source and the second optical fiber.

3. A device according to claim 2, wherein the first end of the first optical fiber and the second end of the second optical fiber are united by a ferrule of transparent material provided with orifices for communication with the environment at cryogenic temperature.

4. A device according to claim 1, comprising a first light source constituted by a laser diode of wavelength λ situated in the infrared and of power lying in the range a few tens of milliwatts to several hundreds of milliwatts for continuously emitting a detection signal via a Y coupler into said second end of the first optical fiber to illuminate the rear face of the palladium micromirror while simultaneously applying localized heating to said rear face, the Y coupler receiving in return the light signal of wavelength λ as reflected by the palladium micromirror and applying said reflected light signal to said detection means.

5. A device according to claim 1, comprising a first light source constituted by a laser diode of wavelength λ situated in the infrared and of power lying in the range a few tens of milliwatts to several hundreds of milliwatts for continuously emitting a detection signal via an optical isolator into said second end of the first optical fiber to illuminate the rear face of the palladium micromirror situated at the first end of the first optical fiber, thereby providing localized heating of said rear face, the light signal of wavelength λ being transmitted through the semitransparent palladium micromirror to a first end of a second optical fiber placed facing the second end of the first optical fiber carrying the palladium micromirror, the second optical fiber having a core of diameter that is equivalent to or greater than the core diameter of the first optical fiber, and, at its second end, applying the light signal transmitted through the palladium micromirror to said detection means.

6. A device according to claim 5, wherein adhesive fixes the first optical fiber close to its first end to a transparent support provided with orifices for communicating with the environment at cryogenic temperature, and wherein adhesive also fixes the second optical fiber close to its first end to the support in such a manner that the distance between the first end of the first fiber and the first end of the second fiber is of the order of a few tens of micrometers.

7. A device according to claim 1, wherein the first optical fiber has a core diameter of about 50 micrometers and a cladding diameter of about 125 micrometers.

8. A device according to claim 1, wherein the palladium micromirror is constituted by a film of thickness lying in the range 10 nm to 50 nm, and preferably in the range 15 nm to 30 nm.

9. A device according to claim 1, wherein the environment at cryogenic temperature is constituted by an atmosphere of gas such as nitrogen.

10. A device according to claim 1, wherein the environment at cryogenic temperature is constituted by a liquid such as a cooling oil.

* * * * *